(12) United States Patent
Laan et al.

(10) Patent No.: US 10,018,466 B2
(45) Date of Patent: Jul. 10, 2018

(54) BRA FITTING METHOD

(71) Applicant: Van De Velde NV, Schellebelle (BE)

(72) Inventors: Dominicus Jozef Laan, BG Driebergen-Rijsenburg (NL); Roel De Rijck, Sint Amandsberg (BE); Michael F. J. Bal, Schellebelle (BE); Sabine M. Dotremont, Schellebelle (BE); Geert Jozef Van Der Biest, Schellebelle (BE); Lieve R. Vermeire, Schellebelle (BE)

(73) Assignee: VAN DE VELDE NV, Schellebelle (BE)

( * ) Notice: Subject to any disclaimer, the term of this patent is extended or adjusted under 35 U.S.C. 154(b) by 344 days.

(21) Appl. No.: 14/784,615

(22) PCT Filed: Apr. 16, 2014

(86) PCT No.: PCT/EP2014/057717
§ 371 (c)(1),
(2) Date: Oct. 15, 2015

(87) PCT Pub. No.: WO2014/170366
PCT Pub. Date: Oct. 23, 2014

(65) Prior Publication Data
US 2016/0076884 A1 Mar. 17, 2016

(30) Foreign Application Priority Data
Apr. 18, 2013 (EP) ..................................... 13164218

(51) Int. Cl.
*A41C 5/00* (2006.01)
*G01B 21/10* (2006.01)
(Continued)

(52) U.S. Cl.
CPC ............ *G01B 21/10* (2013.01); *A41C 3/0028* (2013.01); *A41C 5/00* (2013.01); *A41H 1/00* (2013.01);
(Continued)

(58) Field of Classification Search
CPC .......... A41C 5/00; A41C 3/0028; A41H 1/00; A41H 1/02; A41H 3/00; A41H 3/04;
(Continued)

(56) References Cited

U.S. PATENT DOCUMENTS 1,935,998 A * 11/1933 Strading ................... A41H 1/02
33/15
2,428,980 A * 10/1947 McCann ............... A61B 5/1135
33/514.2
(Continued)

OTHER PUBLICATIONS

International Search Report pertaining to Application No. PCT/EP2014/057717 with an International filing date of Apr. 16, 2014.
(Continued)

*Primary Examiner* — Gloria Hale
(74) *Attorney, Agent, or Firm* — Dinsmore & Shohl LLP (57) ABSTRACT

The present invention relates to a bra fitting method for determining and presenting customized advice for bras. Compared to existing methods the present method is based on an optimized fitting of the bodily dimensions with the functional characteristics of a bra model. Applying a given technique, the present invention incorporates the functional characteristics, and in particular the lifting, shaping and covering of the bra in the brassiere measurement method. As such the method of the present invention results in a customized advice, allowing users to gain insights in the fitting requirements and providing them with a confidence to seek and identify a correctly fitting bra.

9 Claims, 6 Drawing Sheets

Graph 1: Lifting  Graph 2: Shaping  Graph 3: Coverage

Length a  Length b  % Coverage (51) Int. Cl.
  *A41H 1/00* (2006.01)
  *A61B 5/107* (2006.01)
  *G06Q 30/06* (2012.01)
  *A41C 3/00* (2006.01)
  *A61B 5/00* (2006.01)

(52) U.S. Cl.
  CPC .......... *A61B 5/1072* (2013.01); *A61B 5/1073* (2013.01); *A61B 5/1075* (2013.01); *A61B 5/4312* (2013.01); *G06Q 30/0631* (2013.01)

(58) Field of Classification Search
  CPC . A41H 21/00; A41H 5/01; A41H 5/02; G01B 3/1005; G01B 5/107; G01B 5/00; G01B 5/1075; G61B 5/1072; G61B 5/1073
  USPC .................................................. 450/92, 93, 1
  See application file for complete search history.

(56) References Cited

U.S. PATENT DOCUMENTS

| | | | | |
|---|---|---|---|---|
| 5,485,855 A * | 1/1996 | Shiraiwa | ................. | A41H 1/02 33/511 |
| 5,965,809 A * | 10/1999 | Pechter | .................... | A41H 1/02 73/149 |
| 6,336,839 B1 * | 1/2002 | Valli | ........................ | A41C 3/00 450/1 |
| 6,467,180 B1 * | 10/2002 | Chan | ........................ | A41H 1/02 33/17 R |
| 6,665,577 B2 * | 12/2003 | Onyshkevych | ........ | G06Q 30/06 700/130 |
| 7,164,962 B2 * | 1/2007 | Petterson | ............... | G06Q 50/00 700/132 |
| 8,397,391 B2 * | 3/2013 | Ohly | ........................ | A41H 1/02 33/17 R |
| 8,549,763 B2 * | 10/2013 | Krawchuk | ............... | A41B 9/00 2/243.1 |
| 9,568,296 B2 * | 2/2017 | Moore | ..................... | A41H 1/02 |
| 2003/0115110 A1 * | 6/2003 | Yano | ........................ | A41C 5/00 705/26.8 |
| 2007/0066871 A1 * | 3/2007 | Yang | .................. | A61B 1/00096 600/173 |
| 2007/0082579 A1 * | 4/2007 | Baran | ..................... | A41C 3/00 450/77 |
| 2010/0242291 A1 * | 9/2010 | Ohly | ........................ | A41C 3/00 33/17 R |
| 2011/0218876 A1 | 9/2011 | Sorrentino | | |
| 2013/0074353 A1 * | 3/2013 | Petter | ..................... | A41H 1/02 33/512 |
| 2015/0089824 A1 * | 4/2015 | Moore | ..................... | A41H 1/02 33/512 |
| 2015/0342266 A1 * | 12/2015 | Cooper | .................. | A41B 11/00 705/26.7 |
| 2016/0076884 A1 * | 3/2016 | Laan | ........................ | A41H 1/00 702/156 |
| 2016/0260150 A1 * | 9/2016 | Ackerman | ......... | G06Q 30/0621 |
| 2016/0286906 A1 * | 10/2016 | Malal | ..................... | G01C 11/02 |

OTHER PUBLICATIONS

Written Opinion pertaining to Application No. PCT/EP2014/057717 with an International filing date of Apr. 16, 2014.
European Search Report pertaining to Application No. 13164218.3.

* cited by examiner

Graph 1: Lifting     Graph 2: Shaping     Graph 3: Coverage

BRA FITTING METHOD

FIELD OF THE INVENTION

The present invention relates to a bra fitting method for determining and presenting customized size advice for bras. Compared to existing methods the present method is based on an optimized fitting of the bodily dimensions with the functional characteristics of a bra model.

Applying a given technique, the present invention incorporates the functional characteristics, and in particular the lifting, shaping and covering of the bra in the brassiere measurement method. Using said combination of bodily measurements and bra functional characteristics the fitting method further includes a step of graphically presenting the person's brassiere fitting characteristics to the user in a multidimensional space. As such the method of the present invention results in a customized advice, allowing users to gain insights in the fitting requirements and providing them with a confidence to seek and identify a correctly fitting bra.

BACKGROUND TO THE INVENTION

Figure 1:
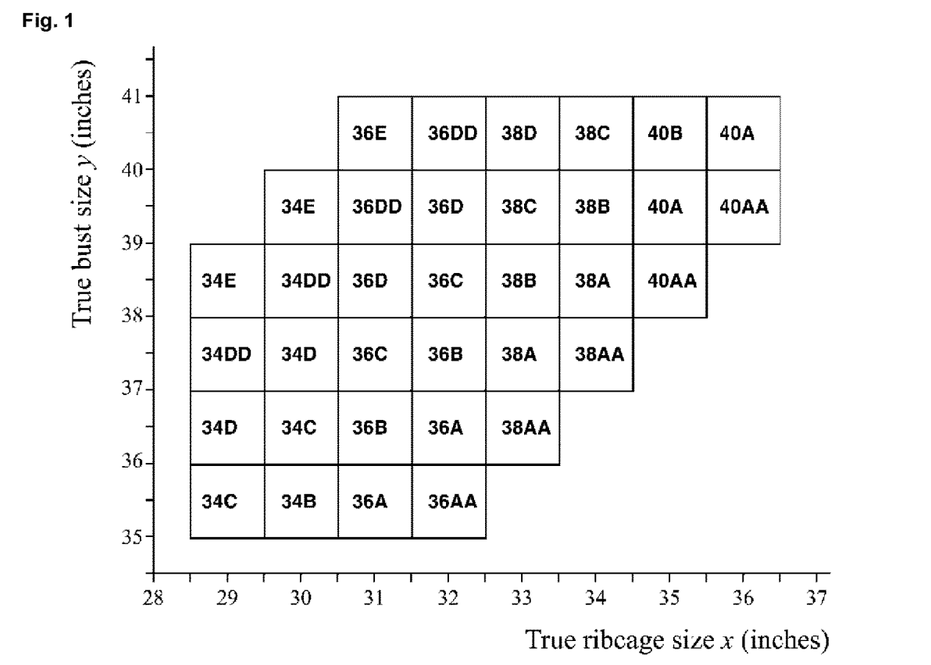
FIG. 1: Example of a custom table based on the measurement of the circumference under the bust and of the circumference over (the fullest part of) the bust.

The invention described herein relates to an innovative method for determining and presenting customized size advice for bras. Existing methods are often based on the use of a custom size table where, based on some body measurements of the person a "best fit" size in the table is selected. An example of such a custom fit table is provided in FIG. 1. In this example on one axis is plotted the circumference under the bust and on the other axis the circumference measured over (the fullest part of) the bust.

In practice however the results in fitting a bra based on these methods is only moderate and, therefore, these existing methods are often not used. The problems associated with these custom tables are due to the fact that one departs from standardized breast shapes and volumes; and that band and cup sizes are not standardized, but vary considerably from one manufacturer to another, resulting in sizes that only provide an approximate fit. A further problem resides in the body measurements used in the foregoing methods. It has been sufficiently proven that they are not decisive for estimating the correct size. Thus, only in about 30% of the cases the correct size is predicted by such a table (see Pechter patent publication U.S. Pat. No. 5,965,809).

Pechter therefore proposed an improved method on the basis of a size below the bust and a size of each breast from the beginning of the breast mound at one side laterally to the parasternal area medially. Where this method, if done properly, would result in a higher correct score, it still departs from standardized breast shapes and volumes. Breasts are often uneven in shape, allowing for one breast to fit better to one size than the other breast. Also measurement of the second body size is difficult to perform, especially with sagging breasts. Another problem is that the method does not provide insight into the fit problem: it is not always the case that a particular size in all respects gives the best fit. A person is in many cases somewhere between two, three or even four bra sizes. One such size might give the best lift, the other size improved shaping and a third size the best coverage. Consequently, bra fitting usually falls back on the "trial and error" method.

In other words, the prior art bra fitting methods;
Have a poor accuracy, and often give in only 30% of the cases a correct answer
Some methods perform better but are difficult to implement.
Methods predict a "best fit" size, but provide no insight into the fit issues.

It is thus an object of the present invention to provide a bra fitting method, that is accurate, easy to implement, and that provides insights into the fit problem of the user. As already mentioned herein above, this is realized by correlating one or more given bodily dimensions, with one or more bra dimensions that are representative for the functional performance of the bra and visualizing said correlation to the user in a multi-dimensional space.

SUMMARY OF THE INVENTION

It is thus an aspect of the present invention to provide a brassiere fitting method comprising; —measuring the torso immediately below the breast; —measuring the breast volumes; —measuring the breast diameters; correlating said torso measurement, breast volume measurements, and breast diameter measurements to one of more functional characteristics of a brassiere, said characteristics being selected from the group consisting of the lifting, shaping and covering characteristics of a brassiere; and visualizing said correlation to the user in a multidimensional space.

In the visualization the bodily dimensions are plotted in a multidimensional space determined by the functional characteristics of the brassiere. In said approach the functional characteristics of the brassiere are translated in measurable parameters, said measurable parameters defining the dimensions of said multidimensional space. As used in the context of the present invention, multidimensional should be read to include all but one dimensional lines, thus including two dimensional planes, three dimensional spaces and n-dimensional ordinary Euclidean spaces. In such a multidimensional space, the bodily measurements will be plotted as a point based on its coordinates, wherein said coordinates are correlated to the dimensions set by the functional characteristics of the brassiere.

As further detailed below, the methods of the present invention are accordingly based on a proper identification, and translation of the functional characteristics of the bra in a measurable parameter that can be directly associated to a bodily measurement of the user. It has thus been found that the lifting characteristics of the brassiere could best be based on the cup volumes and the circumference of the bra when secured. For the shaping characteristics it has been found that the cup volumes and underwire diameter are representative measures, in particular when determined upon exposure to the above mentioned pull force of the brassiere back band. For the covering characteristics the cup volumes and cup surfaces were found to be representative measurable parameters to be used in providing brassiere fitting advice to a user; in particular when combined with the foregoing lifting and shaping characteristics.

Hence, in one embodiment of the method of the present invention the functional characteristics of the bra consist of the lifting, and are based on the cup volumes and the circumference of the bra when secured. In another embodiment of the method of the present invention the functional characteristics of the bra consist of the shaping characteristics of the brassiere, and are based on cup volume and underwire diameter. In an even further embodiment of the present invention the functional characteristics of the bra consist of the covering characteristics of the brassiere, and are based on the cup volumes and cup surfaces. Evidently, the functional characteristics of the brassiere may be combined in the method of the present invention. In one particular embodiment the bodily measurements are correlated to the lifting and shaping characteristics of the brassiere, represented by the cup volumes, the circumference of the bra when secured and the underwire diameter, in particular the underwire diameter when under tension.

As outlined above, the measurable parameters define the dimensions of the multidimensional space wherein the bodily measures will be plotted. Thus for example, in case the brassiere functional characteristics consists of the lifting properties, said lifting properties will be represented by the cup volumes and the circumference of the brassiere when secured, in a two dimensional space with volume (cup volume) and length a (the circumference of the brassiere) as the dimensions. Bodily measures of the user correlating therewith will consist of the breast volumes (volume coordinate in the two dimensional space set by the lifting characteristics of the brassiere) and the circumference (length a coordinate in the two dimensional space set by the lifting characteristics of the brassiere) of the torso immediately below the breast. An example on how these bodily measures are plotted in the two-dimensional 'brassiere lifting' space is provided in FIG. 2. In one embodiment, when plotting the bodily measurements, the breast volumes are expressed as the average volume of the left and right breast volume. In one embodiment the lifting characteristics of the brassiere are represented as the sweet spot value for the cup volumes and the sweet spot value for the circumference of the brassiere. As further detailed hereinafter, the sweet spot corresponds to the average of the functional boundaries of a given brassiere. For the cup volume the sweet spot value is the average of the upper and lower breast volume that can be lifted by the given brassiere. For the circumference of the brassiere, the sweet spot is the average of the upper and lower torso circumference that fits when applying a pull force in the range of about 4-20 Newton to the torso measurement.

Figure 3:
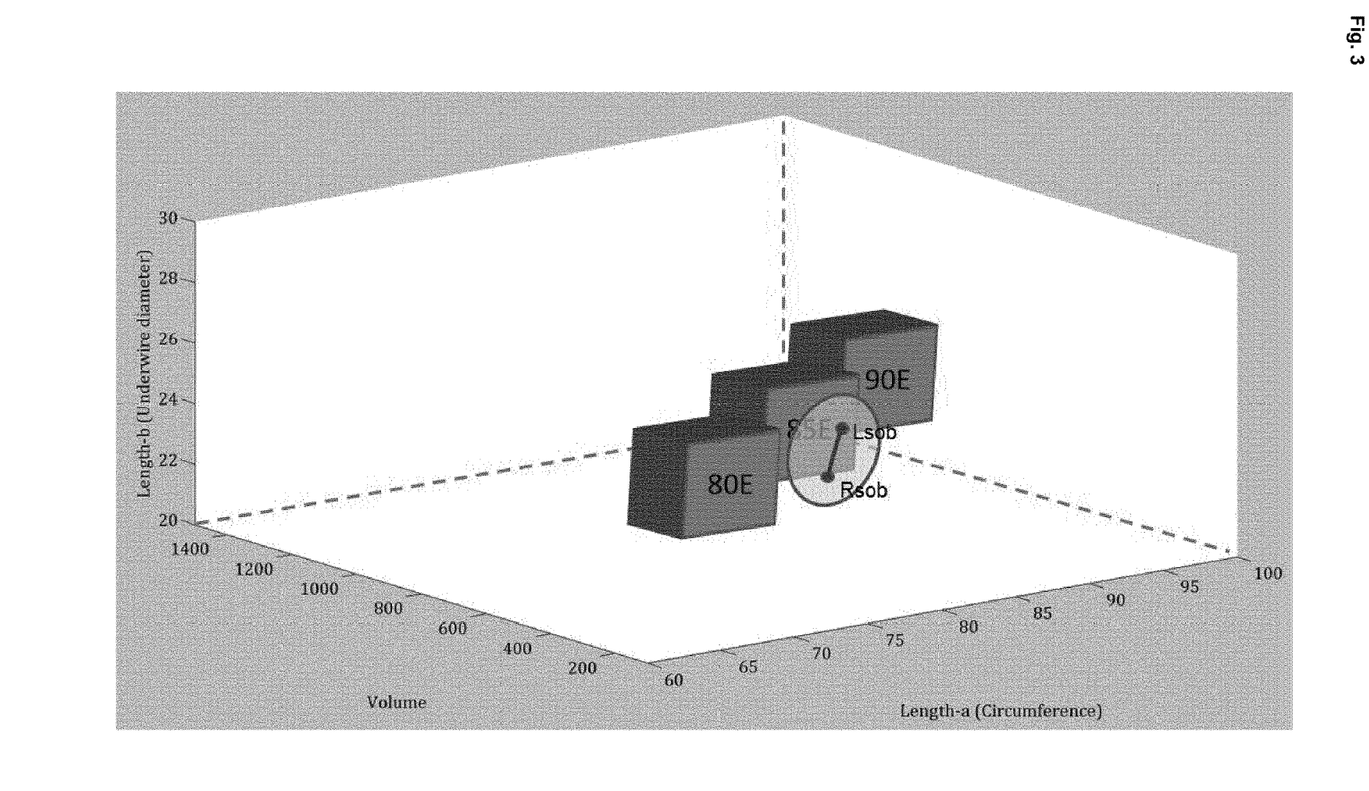

In one embodiment of the present invention, the bodily measurements are correlated to the lifting and shaping characteristics of the brassiere. In said instance the representative and measurable brassiere parameters consist of the cup volumes, the circumference of the brassiere when secured, and the underwire diameter. Instead of a two-dimensional space, the brassiere functional space will now consist of a three-dimensional space with volume (based on the cup volumes), length a (based on the circumference of the brassiere) and length b (based on the underwire diameter) as the dimensions. Bodily dimension measures of the user correlating therewith will consist of the breast volumes (volume coordinate in the three dimensional space set by the lifting and shaping characteristics of the brassiere), the circumference (length a coordinate in the three dimensional space set by the lifting and shaping characteristics of the brassiere) of the torso immediately below the breast, and the breast diameters (length b coordinate in the three dimensional space set by the lifting and shaping characteristics of the brassiere). An example on how these bodily measures are plotted in the three-dimensional 'brassiere lifting' space is provided in FIG. 3. Again and in analogy to the above, in one embodiment the breast volumes are expressed as the average volume of the left and right breast volume. In one embodiment the breast diameters are expressed as the average diameter of the left and right breast diameter. In one embodiment lifting and shaping characteristics are represented as the sweet spot values of the brassiere. For the cup volume the sweet spot value is the average of the upper and lower breast volume that can be lifted by the given brassiere. For the circumference of the brassiere, the sweet spot is the average of the upper and lower torso circumference that fits when applying a pull force in the range of about 4-20 Newton to the torso measurement. For the brassiere diameter, the sweet spot is the average of the upper and lower underwire diameter when applying a pull force in the range of about 4-20 Newton to the underwire.

Figure 4:
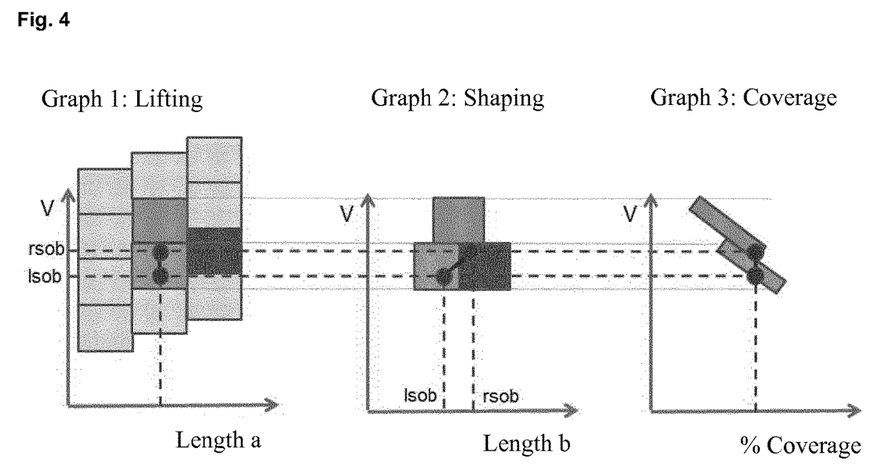
Figure 10:
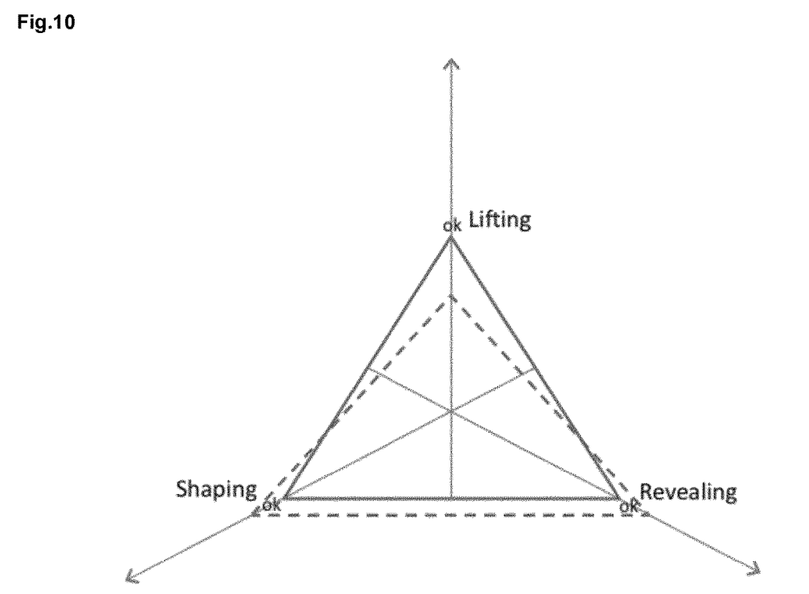
FIG. 10 Further example of bodily measurements plotted in the multidimensional space of the functional bra characteristics for a given bra in accordance with the representation of FIG. 9. In this example the bra does not provide sufficient lifting (bra back too big, . . . ), the bra provides too much shaping (bra cup diameter too small, . . . ), and too much revealing (bra cup surface too small, . . . ).
Figure 11:
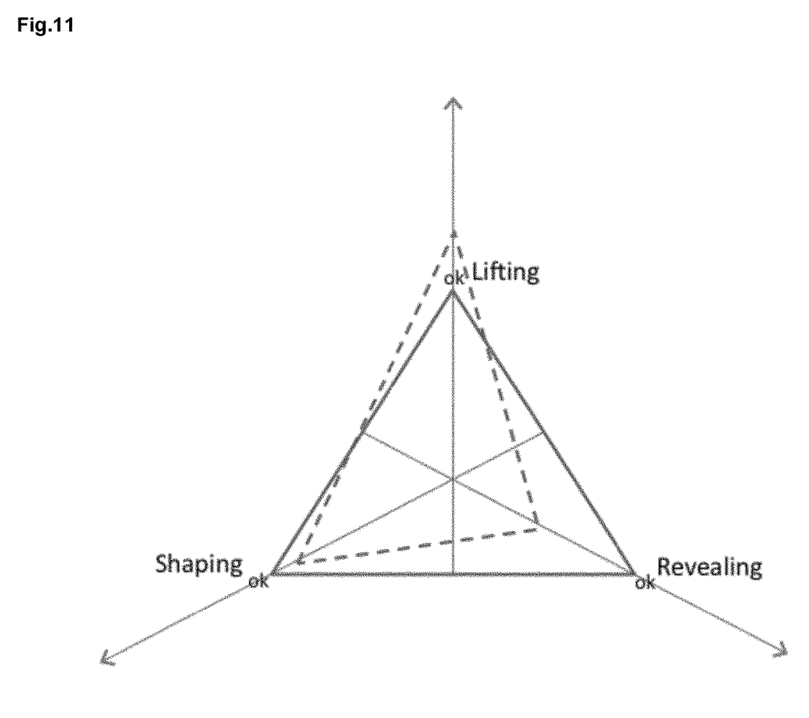
FIG. 11. Using the same parameters as described in FIG. 10, in this example the brassiere provides too much lifting (bra back too small, . . . ). The shaping is OK (cup diameter fits breast diameter, . . . ), but the bra does not provide enough revealing (bra cup surface too big, . . . ).

In an even further embodiment the measurements are correlated to the lifting, shaping and covering characteristics of a brassiere. In said embodiment the representative and measurable brassiere parameters consist of the cup volumes, the circumference of the brassiere when secured, the underwire diameter, and the cup surfaces. The brassiere functional space will now consist of a four-dimensional space with volume (based on the cup volumes), length a (based on the circumference of the brassiere), length b (based on the underwire diameter), and coverage (represented as the percentage of the surface of the parabolic of revolution [the parabolic of revolution is the geometrical space set by the dimensions of the cup] covered by the cup) as the dimensions. Bodily dimension measures of the user correlating therewith will consist of the breast volumes (volume coordinate in the four dimensional space set by the lifting, shaping and covering characteristics of the brassiere), the circumference (length a coordinate in the four dimensional space set by the lifting, shaping and covering characteristics of the brassiere) of the torso immediately below the breast, the breast diameters (length b coordinate in the four dimensional space set by the lifting, shaping and covering characteristics of the brassiere), and the desired % coverage of the breast tissue (coverage coordinate in the four dimensional space set by the lifting, shaping and covering characteristics of the brassiere). A graphical representation of such four-dimensional plot could for example consist of a plurality of two-dimensional graphs with the volume axis as common denominator (see for example FIG. 4). In an alternative embodiment, and taken into consideration the common functional characteristics of a given brassier, the lifting, shaping and covering characteristics of a given brassiere can also be presented in a three dimensional space (see for example FIG. 9) wherein; the lifting is expressed on a first axis; the shaping is expressed on a second axis; and the coverage is expressed on a third axis. The crossings of the solid triangle shown in FIGS. 9 to 11 corresponds to the sweet spot values for a given brassiere.

In said embodiment and for a brassiere with a predetermined and shaped breast volume (the shaped breast volume as used corresponds to the sweet spot value, i.e. the average of the upper and lower breast volume that can be lifted by the given brassiere) the lifting characteristic is based on the determination of a paraboloid of revolution having a diameter equal to the breast diameter and a volume equal to the shaped breast volume. For the thus obtained paraboloid of revolution, the center of gravity is determined relative to the lowest point of the breast fold line (eventually corresponding to the lowest point for the underwire against the torax). The horizontal distance from said center of gravity to the lowest point of the breast fold line corresponds with the radius used in the determination of the rotational momentum caused by gravitation on the shaped breast volume, allowing the calculation of the force in the bra back, needed to lift the shaped breast to its desired position (the position wherein the center of gravity of the lifted breast coincides with the center of gravity of the shaped breast volume). Lift (f_lift) is accordingly correlated with the forces generated in the bra to bring the breast in its desired position, and dependent on;

$$L = f\_\text{lift}(sg, Vb, Hb, Hoa, Hmv, F)$$

Wherein;

sg is the density of the breast tissue

Vb is the volume of the shaped breast volume or the volume of the breasts of the user Hb is the horizontal distance from the center of gravity of the shaped breast to the lowest point of the breast fold line.

Hoa is the height of the underwire at the end of the underarm

Hmv is the height of the underwire at the end of the sternum

F is the force generated by the bra on the cup to lift the breast, mainly through a force in the back (about 80%) and partially (about 20%) by a force in the straps, and directly correlated with the circumference of the bra (Obh), the circumference of the torso immediately below the breast (Op) and the elasticity of the bra back pand (Ebh). In other words F=f_force(Obh, Op, Ebh). Thus even in this embodiment Lifting of the brassiere is function of the volume of the cups (shaped breast volume (Vb)) and length a (the circumference of the brassiere (Obh), wherein these values are correlated with the bodily dimensions consisting of the volume of the breasts of the user (Vb) and of the torso (circumference Op) immediately below the breast of the user, respectively.

In said embodiment and for a brassiere with a predetermined and shaped breast volume (the shaped breast volume as used corresponds to the sweet spot value, i.e. the average of the upper and lower breast volume that can be lifted by the given brassiere) the shaping characteristic is based on a comparison of the paraboloid of revolution determined by the cup volume and cup diameter of a given brassiere, with the paraboloid of revolution having a diameter equal to the breast diameter and a volume equal to the shaped breast volume. In case the paraboloid of revolution determined by the cup equals the paraboloid of revolution determined by the shaped breast the shaping equals 100%. In other words, the shaping (S) is function of;

Dbh is diameter of the cup underwire (in particular when exposed to the typical pull force of the brassiere back band as herein provided)

Vbh is the volume of the cup of the brassiere.

Figure 9:
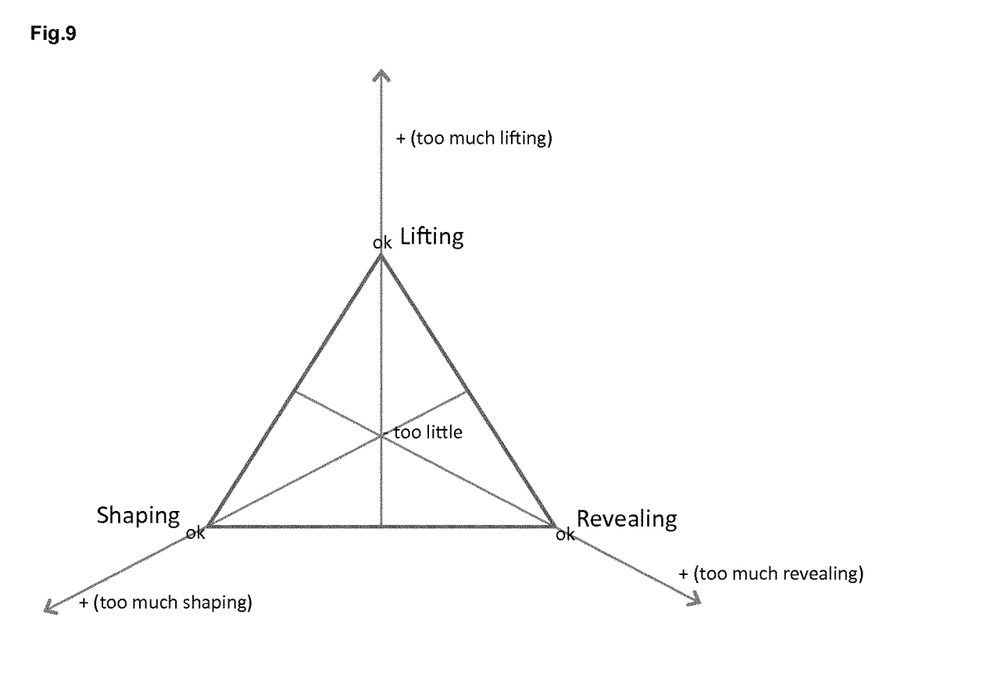

These parameters being used to determine the paraboloid of revolution (i.e. the total surface of the paraboloid of revolution) determined by the cup; and of Db is the breast diameter of the user Vb is the volume of the breast of the user;

These parameters being used to determine the paraboloid of revolution determined by the breast, and wherein the percentage ratio of the paraboloid of revolution determined by the breast over the paraboloid of revolution determined by the cup corresponds to the value for the shaping axis in the 3 dimensional embodiments shown in FIG. 9. The shaping (S) can accordingly be calculated as a shaping function (f-shaping) determined by Db, Vb, Dbh and Vbh, thus represented as S=f_shaping(Db,Vb,Dbh,Vbh). Again, also in this embodiment the Shaping is function of cup volumes (Bbh) and length b (based on the underwire diameter (Dbh)), being correlated with the bodily dimensions consisting of the volume of the breasts of the user (Vb) and the breast diameters (Db) of the users, respectively.

The same paraboloids of revolution described in the foregoing shaping function are used in determining the percentage covering for a given brassiere. In this instance the covering (C) corresponds to the percentage ratio of the paraboloid of revolution determined by the breast over the paraboloid of revolution determined by the cup, but in this instance limited to the proportion of the surface of this paraboloid of revolution that is effectively completed by the bra cup. In the example of FIG. 9, instead of the % coverage the reveal % is used and equals 100% minus the % coverage. In other words, the parameters used in determining the covering (C) are;

Db is the breast diameter of the user

Vb is the volume of the breast of the user;

these parameters being used to determine the paraboloid of revolution determined by the breast of the user; and Obh corresponding to the surface of the bra cup. In one embodiment the surface of the bra cup is simply based on the actual surface of the bra cup pattern, or on the actual surface of the bra foam cup. In another embodiment one takes into consideration the surface of the bra on the shaped breast, and based on the paraboloid of revolution determined by the bra cup as mentioned hereinbefore and accordingly dependent on Dbh the diameter of the cup underwire (in particular when exposed to the typical pull force of the brassiere back band as herein provided), and Vbh the volume of the cup of the brassiere. The covering (C) or reveal (R) can accordingly be calculated as a covering function (f_covering) of a reveal function (f-reveal) determined by Db, Vb, and Obh; thus represented as R=f_reveal (Db,Vb,Obh) or C=f_reveal(Db, Vb, Obh). Thus even in this embodiment the covering function of a brassiere is function of cup volumes (Bbh) and % coverage (based on the cup surface (Obh)) and correlated to the bodily dimensions consisting of the volume of the breasts of the user (Vb) and the surface of the paraboloid of revolution calculated using the volume of the breasts and the diameter of the breasts (Db).

Thus in the methods of the present invention the correlation to lifting characteristics of the brassiere is based on a correlation of breast volumes with cup volumes and of torso measurement with circumference of the bra band. In a preferred embodiment the torso measurement is determined when applying a pull force in the range of about 4-20 Newton, in particular in the range of about 9-17 Newton, more in particular in the range of about 9-14 Newton.

The correlation to shaping characteristics of the brassiere is based on a correlation of breast volumes with cup volumes and of breast diameters with underwire diameters, and the correlation to covering characteristics of the brassiere is based on a correlation of breast volumes with cup volumes and of desired coverage with cup target surface.

In a particular embodiment of the present invention the torso measurement, breast volume measurements, and breast diameter measurements are plotted in a multidimensional space based on the functional characteristics of the brassiere, and consisting of three two-dimensional graphs with the volume y-axis as common denominator, wherein;

a first plot represents the lifting characteristics of the brassiere with length a as x-axis and volume as y-axis, a second plot represents the shaping characteristics of the brassiere with length b as x-axis and volume as y-axis, a third plot representing the covering characteristics of the brassiere with % coverage as x-axis and volume as y-axis;

and wherein volume is based on the cup volumes, length a is based on the circumference of the brassiere, length b is based on the underwire diameter, and coverage is represented as the percentage of the surface of the parabolic of revolution [the parabolic of revolution is the geometrical space set by the dimensions of the cup] covered by the cup.

In this embodiment the bodily measurements are correlated to the lifting, shaping and covering characteristics of a brassiere, by plotting the measurements into the multidimensional space, wherein the torso measurement is plotted on the length a axis, the breast volumes are plotted on the volume y axis, the breast diameters are plotted to the length b axis. Each brassiere has in principle a different target % coverage, and said values are correlated to the desired coverage on the % coverage axis. Alternatively, and in accordance with example provided in FIG. 9, in each of the embodiments of the present invention, % reveal can be used instead of % coverage and equals 100-% coverage.

In another embodiment the lifting, shaping and coverage characteristics of the brassiere are plotted in a multidimensional space, characterized in that said multidimensional space is based on plotting of the brassiere characteristics on a three dimensional graph wherein;
  the lifting characteristics axis of the brassiere corresponds the lift L determined as described hereinbefore,
  the shaping characteristics axis of the brassiere corresponds to the shaping S determined as described hereinbefore, and
  the covering characteristics axis of the brassiere corresponds to the covering C determined as described hereinbefore.

In this embodiment the bodily measurements are correlated to the lifting, shaping, and covering characteristics of a brassiere, by plotting the measurements into the multidimensional space, wherein the L value for the user and based on the volume of the breasts of the user is plotted on the lifting characteristics axis of the brassiere, the S value(s) for the user and based on the paraboloid of revolution determined by the breast(s) of the user is plotted on the shaping characteristics axis of the brassiere, and the C value(s) for the user and based on the paraboloid of revolution determined by the breast(s) of the user is plotted on the covering characteristics axis of the brassiere.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings make apparent to those skilled in the art how the several forms of the invention may be embodied in practice.

FIG. 2: Example of a brassiere lifting space. Y-axis corresponding to the volume dimension set by the volumes of the cups. X-axis corresponding to length a dimensions set by the circumference of the bra when secured. The rectangular gray boxes in said graph represent the functional boundaries of a given brassiere, wherein the white annotated area in the center of said boxes represent the so named 'sweet spot' of the bra, i.e. corresponding to the two dimensional area wherein the lifting characteristics of the given bra are (close to) optimal. The corresponding bodily dimensions of the user are plotted as an overlay in said brassiere lifting space, with spot Lsob based on the volume of the left breast and the circumference (length a coordinate) of the torso immediately below the breast; and spot Rsob based on the volume of the right breast and the circumference (length a coordinate) of the torso immediately below the breast. The elliptic area surrounding the Lsob and Rsob spots represents the search domain for a bra size with proper lifting characteristics.

FIG. 3: Example of a brassiere lifting and shaping space. Y-axis corresponding to the volume dimension set by the volumes of the cups. X-axis corresponding to length a dimensions set by the circumference of the bra when secured. Z-axis corresponding to length b dimensions set by diameter of the bra underwire. The rectangular gray boxes in said graph represent the functional boundaries of a given brassiere, wherein the white annotated area in the center of said boxes represent the so named 'sweet spot' of the bra, i.e. corresponding to the three dimensional area wherein the lifting and shaping characteristics of the given bra are optimal. The corresponding bodily dimensions of the user are plotted as an overlay in said brassiere lifting/shaping space, with spot Lsob based on the volume of the left breast, the circumference (length a coordinate) of the torso immediately below the breast, and the diameter of the left breast (length b coordinate); and spot Rsob based on the volume of the left breast, the circumference (length a coordinate) of the torso immediately below the breast, and the diameter of the right breast (length b coordinate).

FIG. 4: Example of a brassiere lifting, shaping and covering space. Wherein the multidimensional space based on these functional characteristics of the brassiere is represented as a series of three two-dimensional graphs with the volume y-axis as common denominator, wherein;
  a first plot represents the lifting characteristics of the brassiere with length a as x-axis and volume as y-axis,
  a second plot represents the shaping characteristics of the brassiere with length b as x-axis and volume as y-axis,
  a third plot representing the covering characteristics of the brassiere with % coverage as x-axis and volume as y-axis;
and wherein in each of said graphs gray boxes represent the functional boundaries of a given brassiere and wherein in each of said graphs the dimensions of the user are plotted as an overlay with the breast volumes as a common denominator.

FIG. 9: Further example of the multidimensional space for a given brassiere wherein the lifting characteristics (function), shaping characteristics (function), and covering characteristics(function) are normalized based on the optimal value for this characteristic (function). In this graph, coverage is expressed as revealing instead. The ok on each of the axes corresponds to the sweet spot value for the given characteristic of the brassiere at stake. A higher value of the function value for a given person and a given bra size/style indicates that the function is over performed (e.g. too much lifting or too much revealing). Lower values of the function value indicates that the function is under performed (e.g. not enough lifting or not enough revealing). For each brassiere such a functional triangle can be constructed, wherein the functional axes are scaled to the optimal value for the sweet spots of the brassiere.

DETAILED DESCRIPTION OF THE INVENTION

The proposed invention is a method that solves the above-mentioned problems, and is based on a method that takes into consideration the functional characteristics of the bra and fits said functional characteristics to bodily measurements including breast volume as the core measurement. It further provides insight in the fitting requirements of the user by visualizing the correlation of the bodily dimensions to the functional characteristics of the bra in a multidimensional space. As already mentioned hereinbefore, the functional characteristics of the bra are related to the following functions:

lifting: the breast tissue to be lifted by the bra;
shaping: the breast tissue to be shaped to a (usually round) form; and
covering: the breast should be partly covered and partly revealed (percentage depending on the bra style).

These functions will be described hereinafter in more detail.

Lifting

The non-supported breast is pulled down by the force of gravity. The actual sag is dependent on the firmness of the breast tissue and the weight of the breast. The bra lifts the breast mainly through the force in the back (about 80%) and partially (about 20%) by the force in the straps (depending on the bra style). The force is transmitted through the underwire onto the cup and then the breast. The necessary lift force is directly dependent on the weight of the breasts. The weight of the breast is (via the density of breast tissue) directly related to the volume of the breast.

In order to properly fulfill the lifting function, the bra must generate sufficient force in the bra back pand. For this purpose it is necessary that the bra is sufficiently tight to the body, and that the bra back pand generates a minimal pull force when in use. The latter is depending on breast weight and circumference of the body, such as for example in the range of about 4, 5, 6, 7, 8, 9, 10-14, 15, 16, 17, 18, 19, 20 Newton (depending on breast weight and circumference of the body). Consequently, the functional bra characteristic to be considered when evaluating the lifting requirements, includes the circumference of the bra when secured.

In other words, in order to assess the desired lift, a first bodily measure to be taken into account will be the volume of the breast, preferably for each of the breasts individually, and a second bodily measure will be the circumference of the body measured immediately below the breast. Each of said bodily measures will be fit to the lifting characteristics of the brassiere as represented by the cup volume, and the circumference of the bra when exposed to the aforementioned pull force. Evidently, for this second brassiere characteristic, a better correlation can be expected in case the circumference of the body is also assessed, using for example a newton meter and applying a corresponding pull force as expected for the brassiere back band when in use. Thus in a further embodiment of the present invention, the circumference of the body measured immediately below the breast, is determined when applying a pull force equivalent to the pull force expected for the brassiere back band when in use.

Shaping

Further to the lifting of the breast, a further function to be performed by the brassiere consists of shaping the breast tissue in a more or less circular paraboloid. The diameter of the circular base of the paraboloid is determined by the breast diameter and the height of the paraboloid of revolution is determined by the breast volume in combination with the breast diameter. In order to perform the shaping function properly, the bra must comply with two characteristics;

the volume of the cup should fit as closely as possible to the volume of the breast. In case the cup volume is too small, the cup will cut into the breast with loss of the desired shape. In case the cup volume is too large, the cup will be deformed with again a loss of the desired elliptic paraboloid shape;
the diameter of the bra underwire should fit as closely as possible to the diameter of the breast. When considering the diameter of the bra underwire, one preferably takes into account that this diameter may change, it is likely to be pulled open, by the pull force of the bra back pand. In case the diameter of the bra underwire is too small, the bra has the tendency to ride up to the breast tissue, again resulting in a deformation of the desired circular paraboloid shape. In case the diameter of the bra underwire is too large, a space occurs between the bra underwire and the breast tissue and thus a defective fit of the bra to the body.

Thus in determining the desired shape, there must be a fit between the volume and diameter of the breasts with the cup volume and the diameter of the bra underwire respectively. When considering the diameter of the bra underwire, one preferably uses the underwire diameter under tension. As for the circumference of the bra, also the deformation of the bra underwire results from the necessary pull force generated by the bra back pand to lift the breast tissue. It has presently been established that the diameter of the bra underwire and in particular when considered under tension is a good parameter in correlating the bodily dimensions of the user to the functional characteristics of the brassiere when assessing the shaping requirements.

Next to the diameter of the bra underwire, the further functional characteristic of the bra involved in shaping of the breast tissue will be the cup volume. Similar to the remarks regarding the bra underwire diameter, also the cup volume may be affected by the pull force exerted by the back band of the brassiere. Consequently, when correlating the breast volumes of the user to the cup volumes, eventual and expected deformations are preferably taken into account. As such, in the method of the present invention, bra fitting advice regarding the desired shaping of the brassiere will be based on the measurement of the breast volumes and the breast diameters; correlating said bodily measurements to the cup volumes and the bra underwire diameter, preferably when exposed to the above mentioned pull force of the brassiere back band; by means of a graphical representation in a multidimensional space.

Covering

Provided the breast is properly shaped by the brassiere, a further requirement may reside in the breast coverage. Evidently the desired coverage will also be dependent on the bra model. For example, in case of a full bra model the desired coverage will be from about 85% to about 90%, in case of a balconette bra the desired coverage will be from about 75% to about 80%. In case the surface of the cup is too large, this will not only result in an over coverage of the breast, but may also result in deformation (crinkling of the cup) of the cup shape. In case the surface of the cup is too small, this will not only result in a too small coverage of the breast, but typically also results in a cutting of the cup in the breast tissue.

So in order for the bra to properly fulfill its covering function, the surface of the cup will have to amount to a certain 'desired' percentage of the breast as shaped by the bra in the paraboloid of revolution. As already outlined above (Shaping), in providing bra fitting advice to a user the breast volume will be correlated to the cup volumes and accordingly determine the surface of the paraboloid of revolution. Consequently, the expected breast covering by the brassiere will be based on a correlation between the shaped breast volume, preferably for each of the breasts individually and the cup surface. Thus when correlating the bodily dimensions of the users to the functional covering characteristics of the bra, one preferably departs from the shaped volume of the breast tissue for the brassiere of interest. As such each brassiere will have a predetermined coverage of the surface of the paraboloid of revolution. When expressed as a percentage of said surface, this percentage equals the target % coverage of the brassiere.

Bra Fitting Method Using the Aforementioned Functional Bra Characteristics

In the following examples, the method is applied to symmetrical bras, that is to say bras wherein the sizes of the left and right cup are equal. The method is, however, also applicable to asymmetric bras, wherein for the left and right cup in this case, different values are used. Furthermore, in the following examples the method is applied on a non-elastic cup that is to say that the load exercised by the breast does not influence the volume of the cup. The method is also readily applicable to elastic cups, wherein the volume of the cups needs to be determined under load.

As already outlined above, the bra fitting method of the present invention is based on a number of steps, comprising;
- determination of the measurable brassiere parameters representative for one or more functional characteristics of a brassiere, said characteristics being selected from the group consisting of the lifting, shaping and covering characteristics of a brassiere;
- determination of the corresponding bodily dimensions of the user;
- visualizing the user's properties in relation to the functional characteristics of the brassiere, in particular by plotting the user's properties in a multidimensional space set by the measurable brassiere parameters for the selected functional characteristics; and
- interpreting the visualization to provide customized advice to the user.

With reference to the above, the measurable brassiere parameters representative for the lifting behavior consists of the cup volumes and the circumference of the brassiere when secured. For the shaping, it is again based on the cup volumes but now in combination with the diameter of the bra underwire; and for the covering the cup volumes is combined with the surface of the cups. Some details regarding the determination of the brassiere circumference and the diameter of the bra underwire have been given hereinbefore, but evidently these bra characteristics can be determined using a variety of available methodologies, including by measurement or by computer simulation based on properties of materials/underwire/patterns of the bra.

Figure 2:
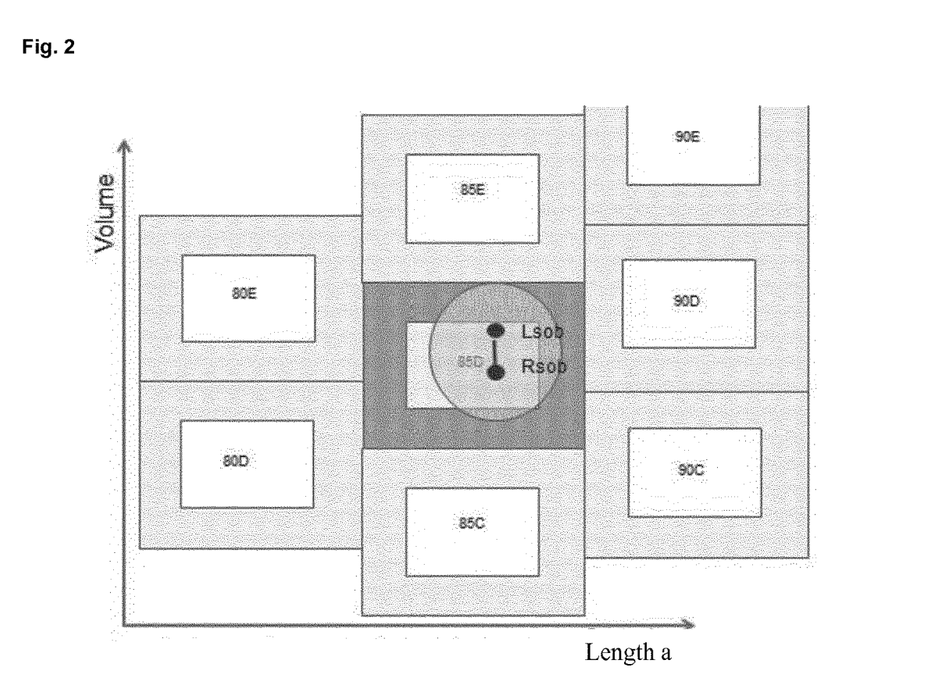

Also the corresponding bodily dimensions, consisting of the breast volumes, breast diameters and circumference of the torso just below the breast, can be determined using art known methods including direct measurement, 3D body scan, photo's and the like Examples on the visualization of the brassiere functional space(s) has been detailed above. In FIG. 2, an example is provided for a brassiere lifting space, with the Lsob and Rsob spot of a user that fit nicely in the sweet spot of a given brassiere annotated 85D. However, in some instances the bodily dimensions of the user would not fit nicely in such a sweet spot. As will become apparent from the following examples, in such instances plotting of the bodily dimensions in the multidimensional space defined by the functional characteristics of the brassiere will provide insight into the fitting problem and result in customized fitting advice to the user.

Example on Fitting of Cup Volume

Figure 5:
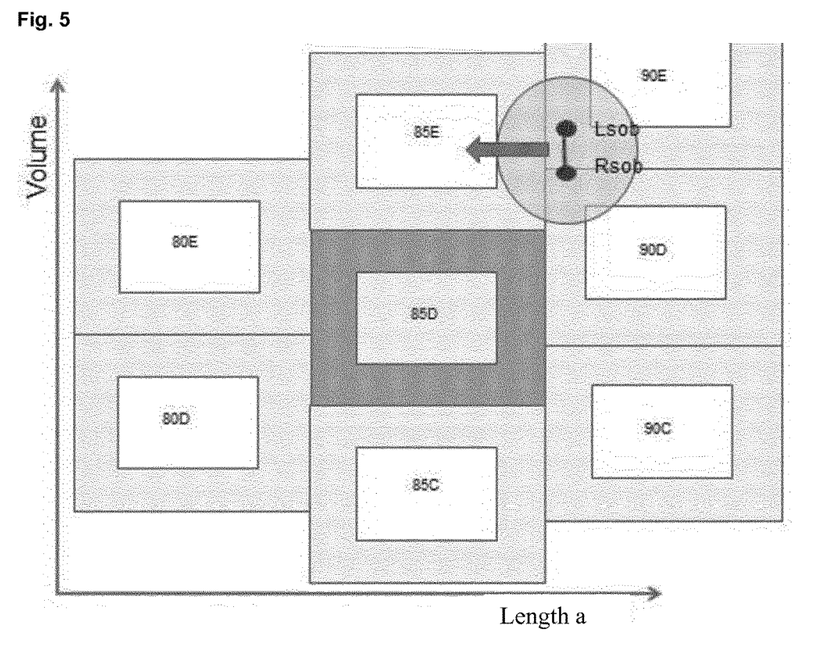
FIG. 5: Further example of the brassiere lifting space as shown in FIG. 2, but now with the overlay plot for a user with breast volumes in-between different brassiere sizes. As explained in the description, the arrow indicates for this user a better fit with brassiere 85E.

FIG. 5 provides an example of the same brassiere lifting space as for FIG. 2, but in this example the bodily dimensions of the user fall outside the sweet spots of the brassieres fitted in said space. The brassieres annotated 90E and 90D would fit with respect to the circumference of the brassiere, but the cup volume for brassiere 90D is too small and the cup volume for brassiere 90E is too large. For the cup volumes a better fit would exist with brassiere 85E. Thus based on the visualization of the bodily dimensions in the brassiere lifting space, we could advice the user to choose brassiere 85E, with the upfront knowledge that this brassiere will be tighter to the body (and thus providing more lift), but possibly this is not a problem for the person.

Figure 6:
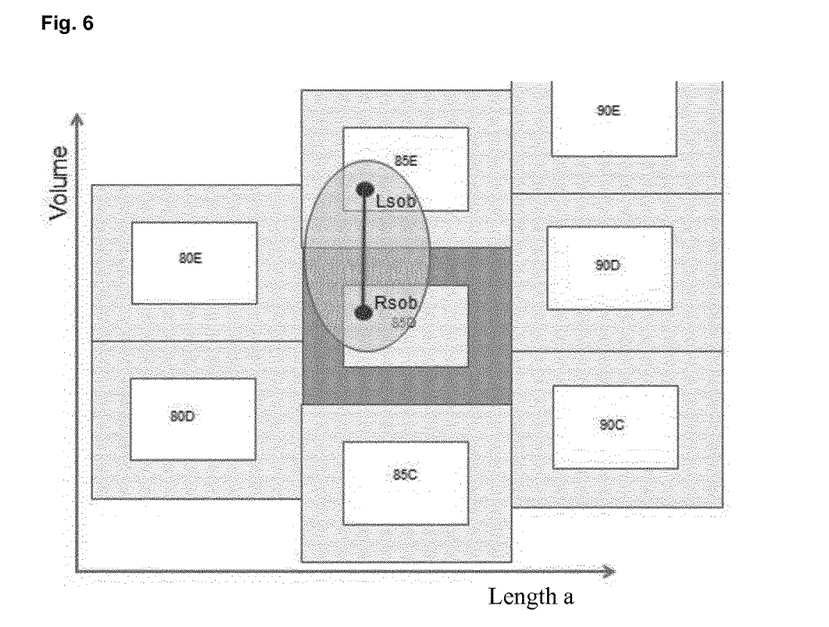
FIG. 6: Further example of the brassiere lifting space as shown in FIG. 2, but now with the overlay plot for a user with two clearly different breast volumes.

In FIG. 6 an example is provided for a user with two clearly different breast volumes. Plotting the bodily dimensions of the user in the brassiere lifting space, it becomes evident that the volume of the left breast falls within the sweet spot of brassiere 85E and that the volume of the right breast falls within the sweet spot of brassiere 85D. In such instance one option could be to choose for brassiere 85E allowing the cups to be at least large enough, with the risk that shaping of the right cup will not be as optimal, or alternatively one could choose for brassiere 80E as the cup volumes better fit with the breasts of the user. Similar to the foregoing example, brassiere 80E will be tighter to the body (and thus providing more lift), but possibly this is not a problem for the person.

Both examples show that plotting of the bodily dimensions in the brassiere functional space provide direct insights in the fitting problems for the user. In the second example, and solely based on the brassiere lifting space, two options remained. Instead of actual trying to fit these two options to the user, the method of the present invention could provide further insight when including further functional characteristics of the brassiere into the equation. In the following example, one further correlates the bodily dimensions of the user to the brassiere shaping space.

Example on Fitting of Shaping

Figure 7:
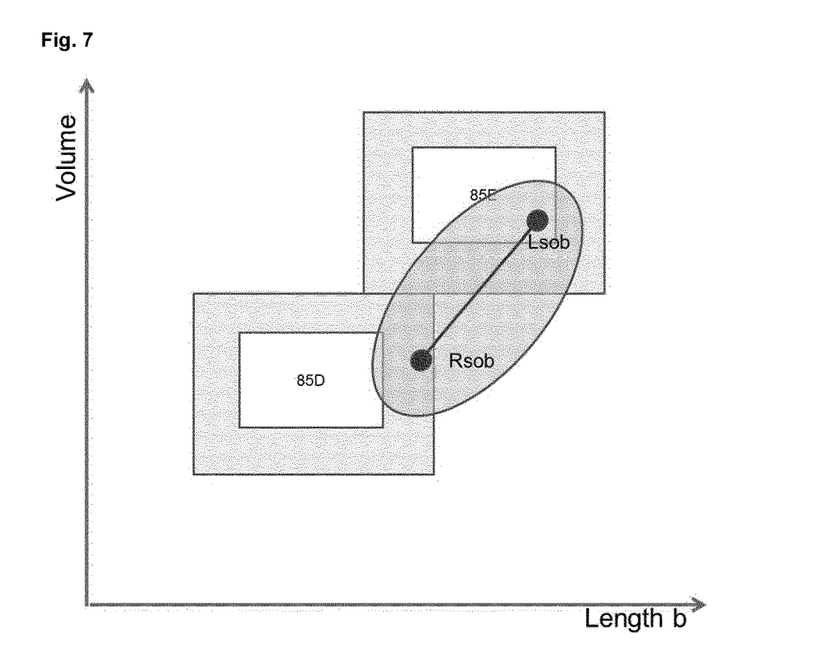
FIG. 7: Further plot of the user of FIG. 6, in the brassier shaping space, demonstrating that for this user brassiere 85E will provide better shaping when compared to brassiere 85D.

In the brassiere functional space the Y-axis corresponds to the volume dimension set by the volumes of the cups. The X-axis corresponding to length b dimensions set by diameter of the bra underwire. The rectangular gray boxes in said graph represent the functional boundaries of a given brassiere, wherein the white annotated area in the center of said boxes represent the so named 'sweet spot' of the bra, i.e. corresponding to the two dimensional area wherein the shaping characteristics of the given bra are optimal. The corresponding bodily dimensions of the user are plotted as an overlay in said brassiere shaping space, with spot Lsob based on the volume of the left breast and the diameter of the left breast (length b coordinate); and spot Rsob based on the volume of the right breast and the diameter of the right breast (length b coordinate).

As evident from FIG. 7, the person with the two different breast volumes has also different breast diameters. In option one above, it was still questioned whether brassiere 85E would not result in a disturbed shaping of the right breast. Since the breast diameter of both breasts is within the functional diameter range of brassiere 85E, the latter is a better choice over brassiere 85D or even 80E, as the underwire diameter of said cups is too small resulting in a tendency of the bra to ride up to the breast tissue, and resulting in a deformation of the desired circular paraboloid shape.

In other words, by plotting the bodily dimensions in a multidimensional space defined by functional characteristics of the brassiere, in the present example based on a combination of lifting and shaping behavior, the method allows to gain full insight in the fitting problems and to provide customized advice to the user.

Example on Fitting of Coverage

Figure 8:
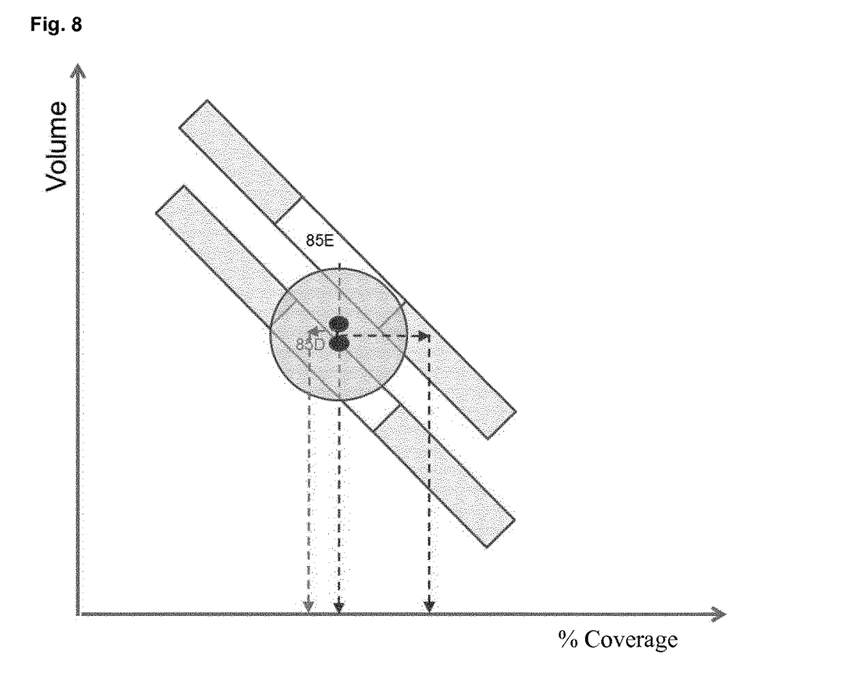
FIG. 8: Further example of the brassiere covering space.

The last example shown in FIG. 8, provides a representation of the brassiere covering space. Again the Y-axis corresponds to the volume dimension set by the volumes of the cups, and the X-axis corresponding to the coverage, represented as the percentage of the surface of the parabolic of revolution [the parabolic of revolution is the geometrical space set by the dimensions of the cup] covered by the cup. The rectangular gray boxes in said graph represent the functional boundaries of a given brassiere, wherein the white annotated area in the center of said boxes represent the so named 'sweet spot' of the bra, i.e. corresponding to the two dimensional area wherein the covering characteristics of the given bra are optimal. The corresponding bodily dimensions of the user are plotted as an overlay in said brassiere shaping space, with spot Lsob based on the volume of the left breast and the desired coverage of the left breast (% coverage coordinate); and spot Rsob based on the volume of the right breast and the desired % coverage of the right breast (% coverage coordinate).

In this example the breast volumes are within the cup volume ranges of both brassiere 85E and 85D, but the coverage of brassiere 85E will be too large. A closer fit in coverage will be provided by brassiere 85D.

Example of Alternative Representation of the Multidimensional Space for the Brassiere Characteristics FIG. 9 provides an alternative representation of the multidimensional space for the brassiere characteristics. Instead of a plurality of two dimensional planes, allowing direct comparison between different brassieres, the functional brassiere characteristics for a given brassiere are plotted in a three dimensional space, wherein the three remaining coordinates, i.e. Lifting (L), shaping (S) and Covering (C) or revealing (R) are calculated for brassiere as described herein.

In this embodiment the bodily measurements are correlated to the lifting, shaping, and covering characteristics of a brassiere, by plotting the measurements into the multidimensional space, wherein the L value for the user and based on the volume of the breasts of the user is plotted on the lifting characteristics axis of the brassiere, the S value(s) for the user and based on the paraboloid of revolution determined by the breast(s) of the user is plotted on the shaping characteristics axis of the brassiere, and the C value(s) for the user and based on the paraboloid of revolution determined by the breast(s) of the user is plotted on the covering characteristics axis of the brassiere.

The bodily measurements are correlated to the lifting, shaping and covering characteristics of a brassiere, by plotting the measurements into the multidimensional space, wherein the torso measurement and breast volumes of the user are used to determine and plot the L-value of the user on the lifting characteristics axis of the brassiere, the breast volumes and breast diameters of the user are used to determine and plot the S-value of the user on the shaping characteristics axis of the brassiere, and breast volumes and breast diameters of the user are used to determine and plot the C-value of the user on the covering characteristics axis of the brassiere.

Instead of plotting the values of each of the breasts, alternatively, the bodily dimensions are plotted using the average breast volumes and/or the average breast diameters.

The invention claimed is:

1. A brassiere fitting method for a user comprising:
measurement of:
  a circumference of a torso of the user immediately below breast(s) of the user;
  breast volumes of the user;
  breast diameters of the user;
correlation of the measurement of the circumference of the torso, the breast volumes, and the breast diameters to one or more functional characteristics of a brassiere, the characteristics being selected from a group consisting of lifting, shaping and covering characteristics of the brassiere; and
visualizing the correlation to the user in a multidimensional space, wherein the measurement of the circumference of the torso, the breast volumes, and the breast diameters are plotted in a multidimensional space determined by the one or more functional characteristics of the brassiere, and consisting of three two-dimensional graphs with a volume Y-axis as a common denominator, wherein;
  a first plot represents the lifting characteristics of the brassiere with length a as x-axis and volume as y-axis,
  a second plot represents the shaping characteristics of the brassiere with length b as x-axis and volume as y-axis,
  a third plot representing the covering characteristics of the brassiere with % coverage as x-axis and volume as y-axis;
and wherein volume is based on cup volumes of the brassiere, length a is based on a circumference of the brassiere, length b is based on an underwire diameter, and % coverage is represented as a percentage of a surface of a parabolic of revolution covered by a cup of the brassiere, wherein the parabolic of revolution is a geometrical space set by dimensions of the cup;

identifying the brassiere as a fitting brassiere when the measurement of the circumference of the torso, the breast volumes, and the breast diameters plotted in the multidimensional space fit within the functional characteristics of the brassiere in the multidimensional space.

2. The method according to claim 1, wherein the length a is based on a circumference of a bra band of the brassiere when secured.

3. The method according to claim 1, wherein the measurement of the circumference of the torso, the breast volumes, and the breast diameters are correlated to the lifting, shaping and covering characteristics of the brassiere by plotting the measurements into the multidimensional space, wherein the measurement of the circumference of the torso is plotted on the length a x-axis, the breast volumes are plotted on the volume y-axis, and the breast diameters are plotted to the length b x-axis.

4. The method according to claim 3, further comprising correlating a desired % coverage of the user to the lifting, shaping and covering functional characteristics of the brassiere, wherein the desired % coverage is plotted to the % coverage x-axis.

5. The method according to claim 1 wherein the one or more functional characteristics of the brassiere are plotted in the multidimensional space on a three dimensional graph wherein:

one L-axis corresponds to L=f_lift (sg, Vb, Hb, Hoa, Hmv, F) wherein F=f_force (Obh, Op, Ebh),
one S-axis corresponds to S=f_shaping (Db, Vb, Dbh, Vbh), and
one C-axis corresponds to C=f_covering (Db, Vb, Obh); and
wherein:
sg is a density of breast tissue of the user,
Vb is a shaped breast volume or a breast volume of the user,
Hb is a horizontal distance from a center of gravity of a shaped breast to a lowest point of a breast fold line of the user,
Hoa is a height of the underwire at an end of an underarm of the user,
Hmv is a height of the underwire at an end of a sternum of the user,
Obh is a circumference of the brassiere,
Op is the circumference of the torso of the user immediately below the breast(s),
Ebh is an elasticity of a bra back band of the brassiere,
Db is a breast diameter of the user,
Dbh is a diameter of a cup underwire of the brassiere,
Vbh is a volume of the cup of the brassiere, and
Obh corresponds to a surface of a bra cup of the brassiere.

6. The method according to claim 5, wherein the one or more functional characteristics of the brassiere are based on sweet spot values for the shaped breast, corresponding to an average of the one or more functional characteristics of the brassiere.

7. The method according to claim 5, wherein the measurement of the circumference of the torso, breast volumes, and breast diameters of the user are plotted into the multidimensional space, wherein:
the measurement of the circumference of the torso and the measurement of the breast volumes of the user are used to determine and plot to the L-axis; and,
the measurement of the breast volumes and the measurement of the breast diameters of the user are used to determine and plot to the S-axis, and
the measurement of the breast volumes and the measurement of the breast diameters of the user are used to determine and plot to the C-axis.

8. The method according to claim 1, wherein the breast diameters are plotted as an average of a left and right breast diameter.

9. The method according to claim 1, wherein the breast volumes are plotted as an average of left and right breast volumes.

* * * * *

UNITED STATES PATENT AND TRADEMARK OFFICE
CERTIFICATE OF CORRECTION

PATENT NO. : 10,018,466 B2
APPLICATION NO. : 14/784615
DATED : July 10, 2018
INVENTOR(S) : Dominicus Jozef Laan et al.

It is certified that error appears in the above-identified patent and that said Letters Patent is hereby corrected as shown below:

Column 5, Line 18:
"pand (Ebh). In other words F=f_force(Obh, Op, Ebh)."
Should read:
--band (Ebh). In other words F=f_force(Obh, Op, Ebh).--; and Column 9, Line 56:
"must generate sufficient force in the bra back pand. For this"
Should read:
--must generate sufficient force in the bra back band. For this--; and Column 9, Line 58:
"body, and that the bra back pand generates a minimal pull"
Should read:
--body, and that the bra back band generates a minimal pull--; and Column 10, Line 37:
"back pand. In case the diameter of the bra underwire is"
Should read:
--back band. In case the diameter of the bra underwire is--; and Column 10, Line 51:
"the bra back pand to lift the breast tissue. It has presently"
Should read:
--the bra back band to lift the breast tissue. It has presently--; and Column 12, Line 40:
"space, we could advice the user to choose brassiere 85E"
Should read:
--space, we could advise the user to choose brassiere 85E--; and Signed and Sealed this
Twenty-ninth Day of January, 2019

Andrei Iancu
*Director of the United States Patent and Trademark Office*

Column 13, Line 52:
"and the desired coverage of the left breast (% coverage"
Should read:
--and the desired % coverage of the left breast (% coverage--.